(12) United States Patent
Trieu

(10) Patent No.: US 6,893,466 B2
(45) Date of Patent: May 17, 2005

(54) INTERVERTEBRAL DISC NUCLEUS IMPLANTS AND METHODS

(75) Inventor: Hai H. Trieu, Cordova, TN (US)

(73) Assignee: SDGI Holdings, Inc., Wilmington, DE (US)

( * ) Notice: Subject to any disclaimer, the term of this patent is extended or adjusted under 35 U.S.C. 154(b) by 100 days.

(21) Appl. No.: 10/253,453

(22) Filed: Sep. 24, 2002

(65) Prior Publication Data

US 2003/0023311 A1 Jan. 30, 2003

Related U.S. Application Data

(62) Division of application No. 09/650,525, filed on Aug. 30, 2000, now Pat. No. 6,620,196.

(51) Int. Cl.$^7$ .................................................. A61F 2/44
(52) U.S. Cl. ................................. 623/17.16; 623/17.11
(58) Field of Search ............................ 623/17.11–17.16

(56) References Cited

U.S. PATENT DOCUMENTS

| | | |
|---|---|---|
| 3,867,728 A | 2/1975 | Stubstad et al. |
| 3,875,595 A | 4/1975 | Froning |
| 4,202,055 A | 5/1980 | Reiner et al. |
| 4,283,799 A | 8/1981 | Pratt, Jr. et al. |
| 4,349,921 A | 9/1982 | Kuntz |
| 4,428,082 A | 1/1984 | Naficy |
| 4,454,612 A | 6/1984 | McDaniel et al. |
| 4,663,358 A | 5/1987 | Hyon et al. |
| 4,772,287 A | 9/1988 | Ray et al. |
| 4,863,477 A | 9/1989 | Monson |
| 4,904,260 A | 2/1990 | Ray et al. |
| 4,911,718 A | 3/1990 | Lee et al. |
| 4,917,704 A | 4/1990 | Frey et al. |
| 5,002,576 A | 3/1991 | Fuhrmann et al. |
| 5,035,716 A | 7/1991 | Downey |
| 5,047,055 A | 9/1991 | Bao et al. |
| 5,071,437 A | 12/1991 | Steffee |
| 5,108,438 A * | 4/1992 | Stone ...................... 623/17.16 |
| 5,147,646 A | 9/1992 | Graham |
| 5,171,280 A | 12/1992 | Baumgartner |
| 5,192,326 A | 3/1993 | Bao et al. |
| 5,306,307 A | 4/1994 | Senter et al. |
| 5,306,308 A | 4/1994 | Gross et al. |
| 5,320,644 A | 6/1994 | Baumgartner |
| 5,443,727 A | 8/1995 | Gagnon |
| 5,534,028 A * | 7/1996 | Bao et al. ................. 623/17.16 |

(Continued)

FOREIGN PATENT DOCUMENTS

| | | |
|---|---|---|
| EP | 0700 671 A1 | 3/1996 |
| WO | WO 90/11740 | 10/1990 |
| WO | WO 95/31946 | 11/1995 |
| WO | WO 9 6/01598 | 1/1996 |
| WO | WO 97/26847 | 7/1997 |
| WO | WO 00/13619 | 3/2000 |
| WO | WO 00/13620 | 3/2000 |

*Primary Examiner*—Alvin Stewart
(74) *Attorney, Agent, or Firm*—Woodard, Emhardt, Moriarty, McNett & Henry LLP

(57) ABSTRACT

Nucleus pulposus implants that are resistant to migration in and/or expulsion from an intervertebral disc space are provided. In one form of the invention, an implant includes a load bearing elastic body surrounded in the disc space by an anchoring, preferably resorbable, outer shell. In certain forms of the invention, the elastic body is surrounded by a supporting member, such as a band or jacket, and the supporting member is surrounded by the outer shell. Kits for forming such implants are also provided. In another form of the invention, an implant is provided that has locking features and optional shape memory characteristics. In yet another aspect of the invention, nucleus pulposus implants are provided that have shape memory characteristics and are configured to allow short-term manual, or other deformation without permanent deformation, cracks, tears, breakage or other damage. Methods of forming and implanting the implants are also described.

32 Claims, 10 Drawing Sheets

U.S. PATENT DOCUMENTS

| | | | |
|---|---|---|---|
| 5,534,030 A | 7/1996 | Navarro et al. | |
| 5,545,229 A | 8/1996 | Parsons et al. | |
| 5,549,679 A | 8/1996 | Kuslich | |
| 5,562,736 A | 10/1996 | Ray | |
| 5,571,189 A | 11/1996 | Kuslich | |
| 5,645,597 A | 7/1997 | Krapiva | |
| 5,674,294 A | 10/1997 | Bainville et al. | |
| 5,674,295 A | 10/1997 | Ray et al. | |
| 5,674,296 A | 10/1997 | Bryan et al. | |
| 5,676,698 A | 10/1997 | Janzen et al. | |
| 5,702,454 A | 12/1997 | Baumgartner | |
| 5,716,416 A | 2/1998 | Lin | |
| 5,755,797 A | 5/1998 | Baumgartner | |
| 5,800,549 A | 9/1998 | Bao et al. | |
| 5,824,093 A | 10/1998 | Ray et al. | |
| 5,863,551 A | 1/1999 | Woerly | |
| 5,865,846 A | 2/1999 | Bryan et al. | |
| 5,888,220 A * | 3/1999 | Felt et al. | 128/898 |
| 5,919,235 A | 7/1999 | Husson et al. | |
| 5,922,024 A | 7/1999 | Janzen et al. | |
| 5,976,186 A | 11/1999 | Bao et al. | |
| 5,990,194 A * | 11/1999 | Dunn et al. | 523/113 |
| 6,001,130 A | 12/1999 | Bryan et al. | |
| 6,022,376 A | 2/2000 | Assell et al. | |
| 6,093,205 A * | 7/2000 | McLeod et al. | 623/17.16 |
| 6,099,565 A | 8/2000 | Sakura, Jr. | |
| 6,110,210 A * | 8/2000 | Norton et al. | 623/17.16 |
| 6,113,639 A | 9/2000 | Ray et al. | |
| 6,132,465 A | 10/2000 | Ray et al. | |
| 6,165,218 A | 12/2000 | Husson et al. | |
| 6,187,048 B1 * | 2/2001 | Milner et al. | 623/17.12 |
| 6,224,630 B1 * | 5/2001 | Bao et al. | 623/17.16 |
| 6,264,695 B1 * | 7/2001 | Stoy | 623/17.16 |
| 6,270,515 B1 * | 8/2001 | Linden et al. | 606/213 |
| 6,270,528 B1 * | 8/2001 | McKay | 623/17.11 |
| 6,428,576 B1 * | 8/2002 | Haldimann | 623/17.16 |
| 6,443,988 B2 * | 9/2002 | Felt et al. | 623/17.12 |
| 2002/0037358 A1 * | 3/2002 | Barry et al. | 427/2.1 |
| 2002/0082636 A1 * | 6/2002 | Sawhney et al. | 606/193 |
| 2004/0107000 A1 * | 6/2004 | Felt et al. | 623/20.32 |

* cited by examiner

INTERVERTEBRAL DISC NUCLEUS IMPLANTS AND METHODS

This application is a divisional of U.S. patent application Ser. No. 09/650,525, filed Aug. 30, 2000, which issued on Sep. 16, 2003 as U.S. Pat. No. 6,620,196.

BACKGROUND OF THE INVENTION

The present invention relates to nucleus pulposus implants and methods for their implantation.

The intervertebral disc functions to stabilize the spine and to distribute forces between vertebral bodies. A normal disc includes a gelatinous nucleus pulposus, an annulus fibrosis and two vertebral end plates. The nucleus pulposus is surrounded and confined by the annulus fibrosis.

Intervertebral discs may be displaced or damaged due to trauma or disease. Disruption of the annulus fibrosis may allow the nucleus pulposus is to protrude into the vertebral canal, a condition commonly referred to as a herniated or ruptured disc. The extruded nucleus pulposus may press on a spinal nerve, which may result in nerve damage, pain, numbness, muscle weakness and paralysis. Intervertebral discs may also deteriorate due to the normal aging process. As a disc dehydrates and hardens, the disc space height will be reduced, leading to instability of the spine, decreased mobility and pain.

One way to relieve the symptoms of these conditions is by surgical removal of a portion or all of the intervertebral disc. The removal of the damaged or unhealthy disc may allow the disc space to collapse, which would lead to instability of the spine, abnormal joint mechanics, nerve damage, as well as severe pain. Therefore, after removal of the disc, adjacent vertebrae are typically fused to preserve the disc space. Several devices exist to fill an intervertebral space following removal of all or part of the intervertebral disc in order to prevent disc space collapse and to promote fusion of adjacent vertebrae surrounding the disc space. Even though a certain degree of success with these devices has been achieved, full motion is typically never regained after such vertebral fusions. Attempts to overcome these problems have led to the development of disc replacements. Many of these devices are complicated, bulky and made of a combination of metallic and elastomeric components. Thus, such devices require invasive surgical procedures and typically never fully return the full range of motion desired.

More recently, efforts have been directed to replacing the nucleus pulposus of the disc with a similar gelatinous material, such as a hydrogel. However, there exists a possibility of tearing or otherwise damaging the hydrogel implant during implantation. Moreover, once positioned in the disc space, many hydrogel implants may migrate in the disc space and/or may be expelled from the disc space through an annular defect, or other annular opening. A need therefore exists for more durable implants, as well as implants that are resistant to migration and/or expulsion through an opening in the annulus fibrosis. The present invention addresses these needs.

SUMMARY OF THE INVENTION

Nucleus pulposus implants that are resistant to migration in and/or expulsion from an intervertebral disc space are provided. Accordingly, in one aspect of the invention, nucleus pulposus implants are provided that include a load bearing elastic body sized for introduction into an intervertebral disc space and surrounded by a resorbable shell that provides the initial fixation for the elastic body within the disc space. The implant may include various surface features on its outer surface, including surface configurations or chemical modifications, that enhance the bonding between the outer surface of the implants and the resorbable shell. Kits for forming such implants are also provided. In other forms of the invention, the elastic body may be surrounded by a supporting member wherein the supporting member is surrounded by the resorbable shell.

In yet another aspect of the invention, nucleus pulposus implants are provided that have shape memory and are configured to allow extensive short-term deformation without permanent deformation, cracks tears or other breakage. In one form of the invention, an implant includes a load bearing elastic body sized for placement into an intervertebral disc space. The body includes a first end, a second end and a central portion wherein the first end and second end are positioned, in a folded, relaxed configuration, adjacent to the central portion to form at least one inner fold. The inner fold preferably defines an aperture. The elastic body is deformable into a second, straightened, non-relaxed configuration for insertion through an opening in an intervertebral disc annulus fibrosis. The elastic body is deformable automatically back into a folded configuration after being placed in the intervertebral disc space. Advantageously, where the implant having shape memory is formed of a hydrogel material, or other, hydrophilic material that may be dehydrated, the implant may be fully or partially dehydrated prior to insertion such that it may be inserted through a relatively small opening in the annulus fibrosis. The opening may, for example, be a pre-existing defect or may be made by making a small incision.

In still other aspects of the invention, nucleus pulposus implants having locking features and optionally having shape memory are provided. In one embodiment, an implant includes a load bearing elastic body having a first end and a second end that are configured for mating engagement with each other. The implant has a first, locked configuration wherein the first and second ends are matingly engaged to each other. The implant may be configured into a second, straightened configuration by application of external force for insertion through an opening in an intervertebral disc annulus fibrosis. When the implant includes shape memory characteristics, it may be automatically configured, or otherwise returned, back into its first, locked configuration after insertion through the opening in the annulus fibrosis and after any external force is removed, or may be placed into its locked configuration by application of external force.

In other aspects of the invention, methods of implanting the nucleus pulposus implants of the present invention are provided. In one mode of carrying out the invention, a method includes providing the appropriate implant, preparing the intervertebral disc space to receive the implant and then placing the implant into the intervertebral disc space. Where the implant includes a load bearing elastic body and an outer resorbable shell, a preferred method includes preparing the intervertebral disc space to receive the implant, introducing the elastic body forming the core of the implant into the disc space wherein the body is surrounded in the disc space by a resorbable outer shell. The material forming the resorbable shell may be placed in the disc space prior to, after, or at the same time as insertion of the elastic body. Alternatively, the elastic body may be surrounded by the outer shell prior to introduction of the elastic body into the intervertebral disc space.

It is an object of the invention to provide nucleus pulposus implants, and kits for their formation, that are resistant to migration in and/or explusion from an intervertebral disc space.

It is a further object of the invention to provide nucleus pulposus implants having shape memory that are configured to allow extensive short term manual, or other deformation without permanent deformation, cracks, tears, breakage or other damage.

It is yet another object of the present invention to provide nucleus pulposus implants having locking features.

It is a further object of the present invention to provide methods of forming and implanting the nucleus pulposus implants described herein.

These and other objects and advantages of the present invention will be apparent from the description herein.

BRIEF DESCRIPTION OF THE FIGURES

FIGS. 14A–14H show side views of top portions of the implants, and FIG. 14I and FIG. 14J show top views of the views shown in 14C and 14D, respectively.

DESCRIPTION OF THE PREFERRED EMBODIMENTS

Figure 1:
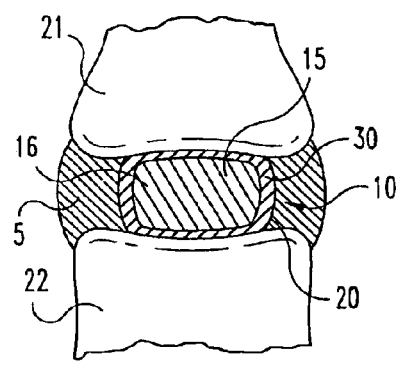
FIG. 1 depicts a side view of a cross-section of a nucleus pulposus implant, including an elastic body 15 surrounded by an anchoring outer shell 30, implanted in the intervertebral disc space of a disc.

For the purposes of promoting an understanding of the principles of the invention, reference will now be made to preferred embodiments and specific language will be used to describe the same. It will nevertheless be understood that no limitation of the scope of the invention is thereby intended, such alterations and further modifications of the invention, and such further applications of the principles of the invention as illustrated herein, being contemplated as would normally occur to one skilled in the art to which the invention relates.

The present invention provides prosthetic intervertebral disc nucleus pulposus implants that may fully or partially replace the natural, or native, nucleus pulposus in mammals, including humans and other animals. In one aspect of the invention, implants are provided that are configured to resist expulsion or other migration through a defect, or other opening, in the annulus fibrosis and to resist excessive migration within an intervertebral disc space. In certain forms, these implants combine the advantages of an injectable/in-situ curing implant with a pre-formed implant. For example, a nucleus pulposus implant may include a load bearing elastic body surrounded by an outer, preferably resorbable or otherwise temporary, shell. The outer shell advantageously anchors the elastic body within the intervertebral disc space. The surface of the elastic body may include various surface features, including various macro-surface patterns, and chemical or physical modifications as described herein to further enhance fixation of the implant to the outer resorbable shell. The surface features, such as the macro-surface patterns and physical modifications, for example, are also expected to enhance fixation of the elastic body to surrounding tissue such that, in certain forms of the invention, no outer shell may be needed.

In other aspects of the invention, nucleus pulposus implants having shape memory that are configured to allow extensive short-term manual or other deformation without permanent deformation, cracks, tears, breakage or other damage are provided. In preferred forms of the invention wherein the implants are formed from a hydrogel or other hydrophilic material, the implants can not only pass through a relatively small incision in the annulus fibrosis, but can also substantially fill and conform to the intervertebral disc space. In one form of the invention, an implant includes a load bearing elastic body with shape memory having first and second ends that are positioned adjacent to a central portion to form at least one inner fold. The inner fold desirably defines an aperture.

In other embodiments of the invention, the shape memory implants are configured to form a spiral or other annular shape in the disc space, and may also be configured to have ends that matingly engage each other for further securing the implant in the disc cavity. Methods of making and implanting the implants described herein are also provided.

Figure 2:
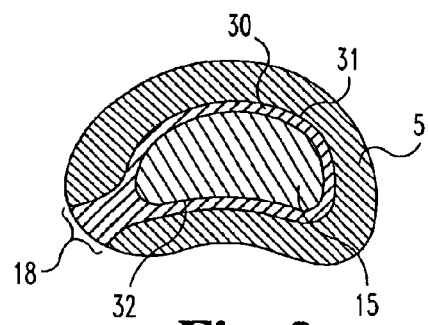
FIG. 2 depicts a top, cross-sectional view of the nucleus pulposus implant of FIG. 1.

As disclosed above, in a first aspect of the invention, a nucleus pulposus implant is provided that includes a load bearing elastic body sized for introduction into an intervertebral disc space and surrounded by an outer, preferably resorbable, shell. Referring now to FIGS. 1 and 2, prosthetic implant 10 includes a core load bearing elastic body 15 disposed in intervertebral disc space 20, between vertebral body 21 and 22 and surrounded by an outer shell 30. More specifically, elastic body 15 has an outer surface 16 in contact with, and preferably bonded to, an outer shell 30 that may advantageously be resorbable, or otherwise temporary. Outer surface 31 of outer shell 30 preferably conforms to the shape of the intervertebral disc space 20, being in contact with annulus fibrosis 5, and may completely surround elastic body 15 as seen in FIGS. 1 and 2, although outer shell 30 may only partially surround elastic body 15. As an example, upper, lower and/or lateral voids surrounding elastic body 15 maybe filled in by outer shell 30, as long as the elastic body is in some way anchored, or otherwise fixed in place, by the outer shell so as to prevent its expulsion from, or excessive migration in, the disc cavity. Thus, outer shell 30 may be configured to fill the aforementioned voids. Additionally, inner surface 32 of outer shell 30 preferably conforms to the shape of elastic body 15, and preferably bonds to outer surface 16 of elastic body 15 as discussed below. In preferred embodiments, the elastic core and the outer shell substantially fill the disc cavity as further discussed below.

Outer shell 30 not only provides for a properly fit implant 10 within intervertebral disc space 20 for maximum load-bearing, stress transfer, and bonding of the implant surface to the surrounding disc tissues for fixation against excessive migration, it also seals an annular defect 18 for further resistance to migration and/or expulsion of the implant. Such sealing of the annular defect may also provide additional physical and mechanical support to the disc. Furthermore, the injectable outer shell material may provide intra-operative flexibility in fitting the core elastic body of implant 10 within the disc space as it may compensate for the differences in geometry and size between the disc space and the pre-formed core.

Figure 3:
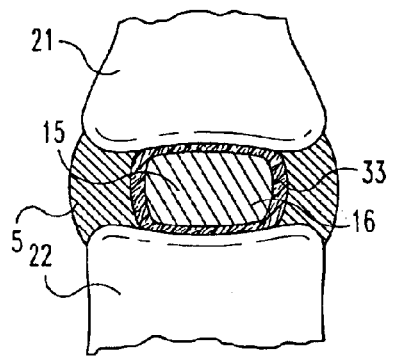
FIG. 3 depicts a side view of a cross-section of the nucleus pulposus implant of FIG. 1 after outer shell 30 has been resorbed and replaced by fibrous scar tissue 33.
Figure 4:
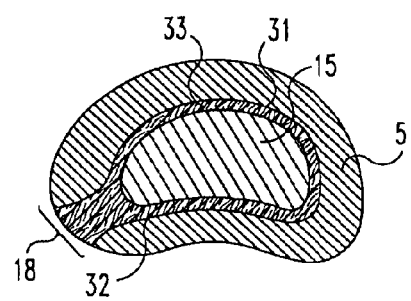
FIG. 4 shows a top, cross-sectional view of the nucleus pulposus implant of FIG. 3.

Outer shell 30 is preferably resorbable and, in such form, is preferably replaced with tissue, such as fibrous tissue and including fibrous scar tissue, that may aid in permanently confining the load bearing elastic body within the disc space. Referring now to FIGS. 3 and 4, tissue 33 has replaced outer shell 30, and thus surrounds elastic body 15. Although elastic body 15 may be confined within the disc space with the aid of tissue 33, body 15 is expected to have some mobility for normal biomechanics.

The dimensions of load bearing elastic body 15 may vary depending on the particular case, but elastic body 15 is typically sized for introduction into an intervertebral disc space. Moreover, elastic body 15 is preferably wide enough to support adjacent vertebrae and is of a height sufficient to separate the adjacent vertebrae. In order to provide long-term mechanical support to the intervertebral disc, the volume of elastic body 15 in the disc space should be at least about 50%, preferably at least about 70%, further preferably at least about 80% and more preferably at least about 90% of the volume of the entire disc space, the remaining volume occupied by outer shell 30. However, the volume of elastic body 15 may be as large as about 99% of the volume of the intervertebral disc space, and thus about 99% of the volume of implant 10. Accordingly, the volume of outer shell 30 may be at least about 1% of the volume of the implant, but may range from about 1% to about 50%. The appropriate size of implant 10 desired in a particular case may be determined by distracting the disc space to a desired level after the desired portion of the natural nucleus pulposus and any free disc fragments are removed, and measuring the volume of the distracted space with an injectable saline balloon. The disc volume can also be measured directly by first filling the disc space with a known amount of the outer shell precursor material.

Figure 12:
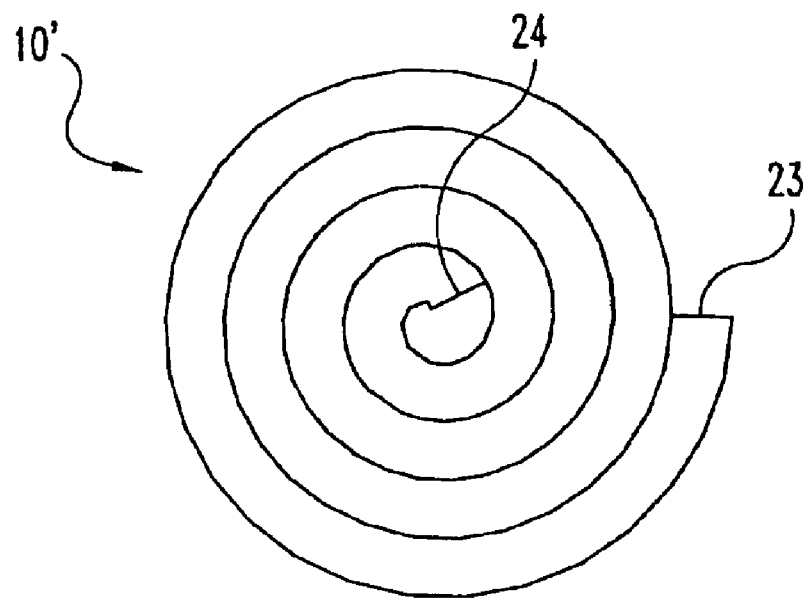
FIG. 12 depicts a top view of an alternative embodiment of a nucleus pulposus implant having shape memory.
Figure 13:
FIG. 13 shows a side view of the implant shown in FIG. 12.
Figure 14A:
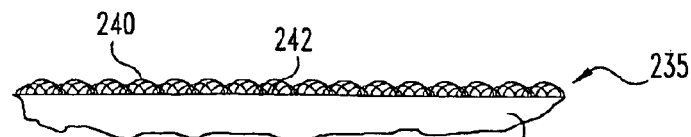
FIGS. 14A–14J depict portions of nucleus pulposus implants with surface modifications.
Figure 14B:
Figure 14C:
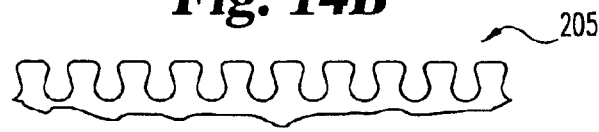
Figure 14D:
Figure 14E:
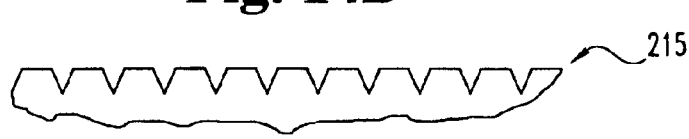
Figure 14F:
Figure 14G:
Figure 14H:
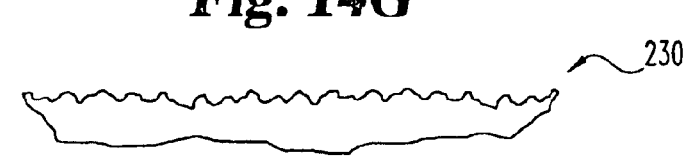
Figure 14I:
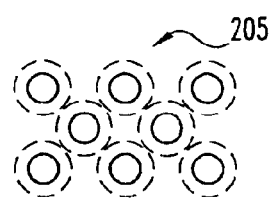
Figure 14J:
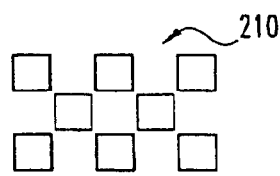

Elastic body 15 may be fabricated in a wide variety of shapes as desired, as long as the body can withstand spinal loads and other spinal stresses. The non-degradable and preformed elastic body 15 may be is shaped, for example, as a cylinder, or a rectangular block. The body may further be annular-shaped. For example, implant 10' in FIGS. 12 and 13 has a spiral, or otherwise coiled, shape. The implant includes a first end 23 and a second end 24. Elastic body 15 may also be shaped to generally conform to the shape of the natural nucleus pulposus, or may be shaped as further described below. Although elastic body 15 is shown as one piece in, for example, FIGS. 1–4, it may be made from one or several pieces.

Elastic body 15 may be formed for a wide variety of biocompatible polymeric materials, including elastic materials, such as elastomeric materials, hydrogels or other hydrophilic- polymers, or composites thereof. Suitable elastomers include silicone, polyurethane, copolymers of silicone and polyurethane, polyolefins, such as polyisobutylene and polyisoprene, neoprene, nitrile, vulcanized rubber and combinations thereof. The vulcanized rubber described herein may be produced, for example, by a vulcanization process utilizing a copolymer produced as described, for example, in U.S. Pat. No. 5,245,098 to Summers et al. from 1-hexene and 5-methyl-1,4-hexadiene. Suitable hydrogels include natural hydrogels, and those formed from polyvinyl alcohol, acrylamides such as polyacrylic acid and poly (acrylonitrile-acrylic acid), polyurethanes, polyethylene glycol, poly(N-vinyl-2-pyrrolidone), acrylates such as poly (2-hydroxy ethyl methacrylate) and copolymers of acrylates with N-vinyl pyrrolidone, N-vinyl lactams, acrylamide, polyurethanes and polyacrylonitrile, or may be other similar materials that form a hydrogel. The hydrogel materials may further be cross-linked to provide further strength to the implant. Examples of polyurethanes include thermoplastic polyurethanes, aliphatic polyurethanes, segmented polyurethanes, hydrophilic polyurethanes, polyether-urethane, polycarbonate-urethane and silicone polyether-urethane. Other suitable hydrophilic polymers include naturally-occurring materials such as glucomannan gel, hyaluronic acid, polysaccharides, such as cross-linked carboxyl-containing polysaccharides, and combinations thereof. The nature of the materials employed to form the elastic body should be selected so the formed implants have sufficient load bearing capacity. In preferred embodiments, a compressive strength of at least about 0.1 Mpa is desired, although compressive strengths in the range of about 1 Mpa to about 20 Mpa are more preferred.

Outer shell 30 may be formed from a wide variety of biocompatible, preferably elastic, elastomeric or deformable natural or synthetic materials, especially materials that are compatible with elastic body 15. The outer shell materials preferably remain in an uncured, deformable, or otherwise configurable state during positioning of the elastic body in the interverterbral disc space, and should preferably rapidly cure, become harder or preferably solidify after being introduced into the intervertebral disc space, or, in other embodiments, prior to positioning of the elastic body in the intervertebral disc space. In preferred embodiments, the outer shell materials may remain deformable after they harden or otherwise solidify. Suitable materials that may be used to form the outer shell include tissue sealants or adhesives made from natural or synthetic materials, including, for example, fibrin, albumin, collagen, elastin, silk and other proteins, polyethylene oxide, cyanoacrylate, polylactic acid, polyglycolic acid, polypropylene fumarate, tyrosine-based polycarbonate and combinations thereof. Other suitable materials include demineralized bone matrix. These precursor materials may be supplied in liquid, solution or solid form, including gel form.

Elastic body 15 may include a variety of surface features on outer surface 16, including chemical modifications and surface configurations, to provide surface features that advantageously improve the bonding between outer surface 16 of the elastic body and inner surface 32 of outer shell 30. In one form of the invention, outer surface 16 is chemically modified utilizing, for example, chemical groups that are compatible with the materials used to form outer shell 30. Suitable chemical modifications include, for example, surface grafting of reactive functional groups, including hydroxyl, amino, carboxyl and organofunctional silane groups. The groups may be grafted by methods known to the skilled artisan. Other modifications include pre-coating with a primer, preferably one that is compatible with the outer shell material, such as a layer of adhesive, sealing or other materials used for forming the outer shell described above.

In yet another form of the invention, elastic body 15 may include a wide variety of surface configurations, such as macro-surface patterns, or protuberances, as seen in FIGS. 14A–14J, showing side views or top views of top portions of elastic bodies with various surface features. Referring now to FIGS. 14A–14J, the pattern may be a dove-tail pattern 200, a circular pattern 205, a square pattern 210, a conical pattern 215, various wave patterns 220 and 225 and random, irregular patterns 230. In other embodiments, a fiber 240 may be disposed in elastic body 241 and may project from the surface 242 thereof to form a fibrous pattern 235. Fiber 240 may be disposed as a loop projecting from the surface of the elastic body, its ends may project from the surface of the elastic body, or the fiber may have a wide variety of other appropriate configurations. The fiber may be a short, polymeric fiber, such as one that is cut to less than about one inch. The fiber may, alternatively, be a continuous polymeric fiber. The fiber may further be braided, and may be woven or non-woven. The macro-surface patterns are preferably formed during formation of elastic body 15. However, outer surface 16 of elastic body 15 may also be physically modified after formation of elastic body 15 by, for example, laser drilling or thermal deformation. Physical modifications include, for example, a microtexturized surface formed by bead-blasting, plasma etching or chemical etching. Procedures for modifying various surfaces in this manner are well known in the art.

In certain forms of the invention, the implant may include only elastic body 15 having one or more of the outer surface features as described above, without the outer resorbable shell. The surface features are expected to provide a certain level of fixation to the surrounding tissues for improved resistance to migration and/or expulsion.

Figure 5:
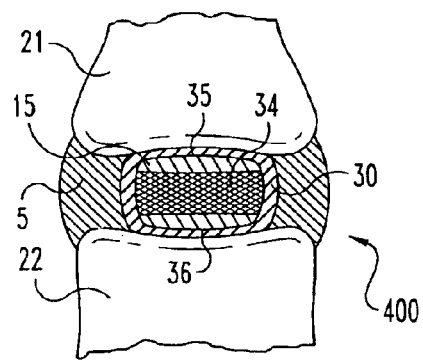
FIG. 5 shows a side view of a cross-section of a nucleus pulposus implant, including an elastic body 15 surrounded by a supporting member 34, in the form of a band, wherein the supporting member is surrounded by an anchoring outer shell 30, implanted in the intervertebral disc space of a disc.

In yet other forms of the invention, the implant may include an elastic body that is surrounded by a supporting, or otherwise constraining, member wherein the supporting member is surrounded by a resorbable shell as described herein. Referring now to FIG. 5, implant 400 includes a load bearing elastic body 15 that is surrounded by a supporting member 34. In one form, supporting member 34 may be a preferably flexible, peripheral supporting band that is disposed circumferentially about elastic body 15 as seen in FIG. 5, leaving upper and lower surfaces 35 and 36, respectively, of elastic body 15 free from the supporting band.

As seen in FIG. 5, portions of upper and lower surfaces 35 and 36, respectively, of elastic body 15 are exposed to directly contact outer shell 30. This exposure minimizes the amount of material needed to construct the supporting member, yet still effectively provides, for example, lateral support. Although the amount of the upper and lower surfaces of elastic body 15 that are exposed may vary, typically at least about 50%, preferably at least about 70%, more preferably at least about 80% and most preferably at least about 90% of the surfaces are exposed.

Figure 6:
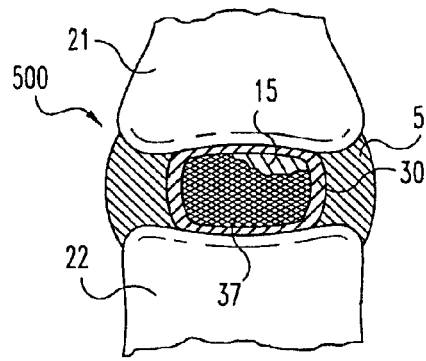
FIG. 6 depicts a side view of a cross-section of a nucleus pulposus implant, including an elastic body 15 surrounded by a supporting member 37, in the form of a jacket, wherein the supporting member is surrounded by an anchoring outer shell 30, implanted in the intervertebral disc space of a disc.
Figure 7A:
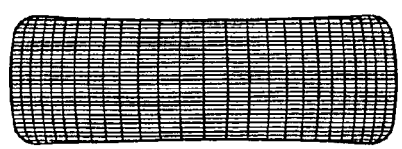
FIGS. 7A–7D depict various patterns of a supporting member of the present invention.
Figure 7B:
Figure 7C:
Figure 7D:
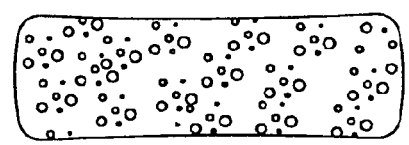

In yet another embodiment shown in FIG. 6, nucleus pulposus implant 500, that includes elastic body 15 as described above, is reinforced with supporting member 37, which takes the form of a jacket. The jacket preferably completely surrounds elastic body 15.

Suitable supporting members, including reinforcing outer bands, covers, or other jackets, may be formed from a wide variety of biocompatible polymers, metallic materials, or combination of materials that form a strong but flexible support to prevent excessive deformation, including lateral (horizontal) deformation, of the core under increasing compressive loading. Suitable materials include non-woven, woven, braided, or fabric materials made from polymeric fibers including cellulose, polyethylene, polyester, polyvinyl alcohol, polyacrylonitrile, polyamide, polytetrafluorethylene, polyparaphenylene terephthalamide, and combinations thereof. Other suitable materials include non-reinforced or fiber-reinforced elastomers such as silicone, polyurethane, copolymers of silicone and polyurethane, polyolefins, including polyisobutylene and polyisoprene, neoprene, nitrile, vulcanized rubber, and combinations thereof. In a preferred form of the invention, a combination, or blend, of silicone and polyurethane is used. Furthermore, the vulcanized rubber is preferably produced as described above for the nucleus pulposus implants. Supporting members 34 and 37 are advantageously made from a porous material, which, in the case of an elastic body made from a hydrogel, or other hydrophilic material, allows fluid circulation through the elastic core body to enhance pumping actions of the intervertebral disc. Supporting members may further be formed from carbon fiber yarns, ceramic fibers, metallic fibers or other similar fibers as described, for example, in U.S. Pat. No. 5,674,295.

FIGS. 7A–7D show supporting bands of various patterns, typically 30 made from various braided materials (bands 25, 26 and 27), or porous materials (band 28), as described above. It is also understood the jackets may also be formed of such patterns. It is realized that the braided materials may also be porous.

Supporting members 34 and 37 preferably decrease lateral deformation, compared to deformation of an implant without the supporting member, as desired. Supporting members 34 and/or 37 may, for example, decrease lateral deformation by at least about 20%, preferably at least about 40%, more preferably by at least about 60% and most preferably by at least about 80%. An implant, such as one that includes an elastic body, having such a supporting member will be flexible and otherwise resilient to allow the natural movements of the disc and provides shock absorption capability at low to moderate applied stress, but will resist excessive deformation for disc height maintenance under high loading conditions. As described herein in the case of a lumbar disc, for example, low applied stress includes a force of about 100 Newtons to about 250 Newtons moderate stress includes a force of about 250 Newtons to about 700 Newtons, and high loading conditions, or high stress, includes a force of above about 700 Newtons. In preferred forms of the invention, the supporting member is flexible, in that it may be folded, or otherwise deformed, but is substantially inelastic, so that the implant is more fully reinforced or otherwise supported.

The elastic body may be covered by the jacket supporting member, or the band supporting member may be wrapped around the circumference of the elastic body. In a form of the invention wherein the elastic body is formed from a hydrogel, or similar hydrophilic material, the hydrogel may be dehydrated a desired amount prior to being covered by the jacket, or prior to wrapping the band around the circumference of the hydrogel body. The hydrogel elastic body may be exposed to saline outside of the body, or may be inserted into the disc space wherein it will be exposed to body fluids in situ, and the body will absorb water and swell. In reference to the peripheral band supporting member, the swelling or expansion of the hydrogel elastic body in the horizontal direction is controlled by the amount of slack designed in the band. After the limited allowable horizontal expansion is reached, the elastic body is forced to expand mostly in the vertical direction until reaching equilibrium swelling under the in vivo load. As the upper and lower surfaces of the elastic body are not substantially constrained, the vertical expansion is mainly controlled by the applied stress and the behavior of the hydrogel material.

Figure 8:
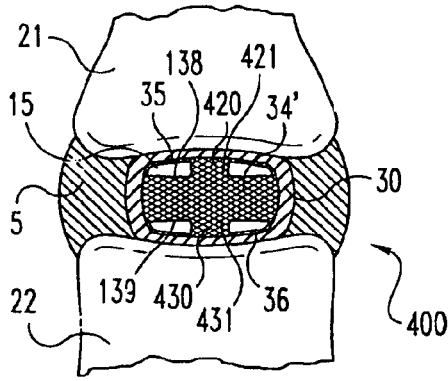
FIG. 8 depicts a side view of a cross-section of a nucleus pulposus implant including an elastic body 15 surrounded by a supporting member 34, taking the form of a band, that is further reinforced, or otherwise supported, by straps 420 and 430. The implant is surrounded by an anchoring outer shell 30 and is shown implanted in the intervertebral disc space of a disc.
Figure 9:
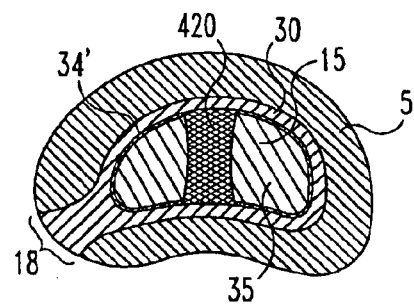
FIG. 9 shows a top, cross-sectional view of the nucleus pulposus implant of FIG. 8.
Figure 10:
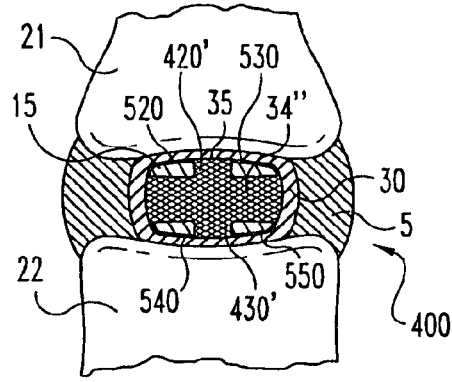
FIG. 10 depicts a side view of an alternative embodiment of a nucleus pulposus implant of the present invention that includes peripheral supporting band 34" and securing straps 520, 530, 540 and 550 and is surrounded by an anchoring outer shell 30 and implanted in the intervertebral disc space of a disc.
Figure 11:
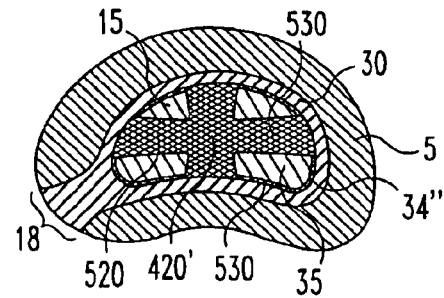
FIG. 11 depicts a top, cross-sectional view of the nucleus pulposus implant of FIG. 10.

In yet other forms of the invention, an implant reinforced with a peripheral supporting band as described above that is surrounded by a resorbable outer shell may be further reinforced with one or more straps. The straps may be advantageous in preventing the peripheral supporting band described herein from slipping, or otherwise sliding off the implant. Referring now to FIGS. 8 and 9, at least one strap 420 extends along upper surface 35 and at least one strap 430 extends along lower surface 36 of elastic body 15 of implant 400. Ends 421 of strap 420 and ends 431 of strap 430 are each preferably connected, or otherwise attached, to peripheral supporting band 34'. The point of attachment may be any location that will secure the strap, including at the upper margins 138 of the band, lower margins 139 of the band or any region between the upper and lower margins. Although two straps 420 and 430 are shown extending along upper surface 35 and lower surface 36, respectively, in FIGS. 8 and 9, one continuous strap may be utilized that extends completely around the implant, or the strap utilized may be in one, two or multiple pieces, as long as the combination of straps are sufficient to prevent excessive slipping and or sliding of the supporting band. Furthermore, more than one strap may extend along upper surface 35 and more than one strap may extend along lower surface 36 of elastic body 15, as seen, for example, in FIGS. 10 and 11 of implant 500, wherein straps 520, 530, 540 and 550 are shown attached, or otherwise connect to supporting member 34". It is realized that the straps may be present in one or more pieces. For example, straps 520 and 530 may form a single strap, as may straps 540 and 550, or may all combine to form a single strap.

In other aspects of the invention, kits designed for forming the intervertebral disc nucleus pulposus implants that include the outer shell described above are provided. In one form, a kit may include a load bearing elastic body as described above, along with a container of material to form the outer, preferably resorbable, shell. The material may be selected from the materials as described above. Moreover, the container that houses the material that forms the shell may be made from a wide variety of materials that are compatible with the outer shell material, including glass and plastic. The kit may further include a supporting member, such as a supporting band, jacket or other outer cover as described above. Generally, the kits include sterile packaging which secures the kit components in spaced relation from one another sufficient to prevent damage of the components during handling of the kit. For example, one may utilize molded plastic articles known in the art having multiple compartments, or other areas for holding the kit components in spaced relation.

Figure 15A:
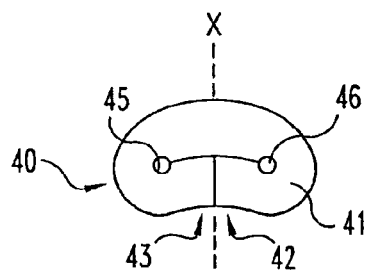
FIGS. 15A–15N show top views of alternative embodiments of nucleus pulposus implants having shape memory in folded, relaxed configurations.
Figure 16A:
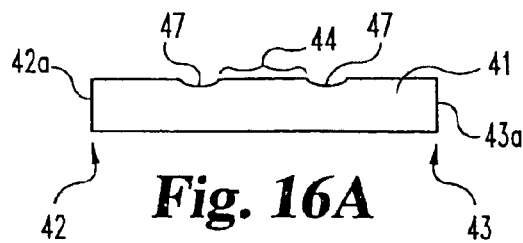
FIGS. 16A–16N depict top views of the implants shown in FIGS. 15A–15N, respectively, in unfolded, non-relaxed configurations.
Figure 16B:

In a further aspect of the invention, nucleus pulposus implants are provided having shape memory that are configured to allow extensive short-term manual, or other, deformation without permanent deformation, cracks, tears, breakage or other damage, that may occur, for example, during placement of the implant into an intervertebral disc space. Referring now to FIGS. 15A and 16A, in one form of the invention, implant 40 includes a load bearing elastic body 41 with shape memory and having a first end 42 and a second end 43 that are positioned adjacent to a central portion 44 to form at least one inner fold 45. Inner fold 45 preferably defines at least one aperture 46 which is advantageously arcuate. The elastic body is deformable, or otherwise configurable, manually, for example, from this first folded, or otherwise relaxed configuration shown in FIG. 15A into a second, substantially straightened, or otherwise non-relaxed configuration shown in FIG. 16A for placement into the intervertebral disc space. As elastic body 41 has shape memory, it returns by itself, automatically, back into the first folded, relaxed configuration once manual or other force is no longer exerted on the body. These implants therefore provide improved handling and manipulation characteristics in that they may be deformed, configured and otherwise handled by an individual without resulting in any breakage or other damage to the implant.

Figure 15B:
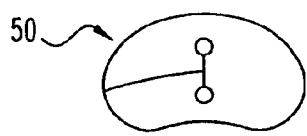
Figure 15C:
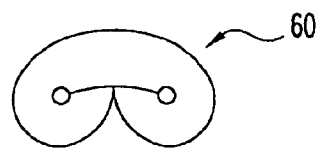
Figure 16C:
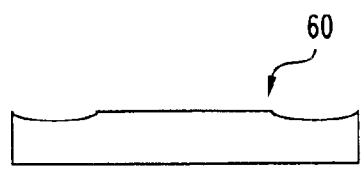

Further describing the shape memory nucleus prosthesis implant 40, implant 40 includes surface depressions 47, or other surface irregularities as more fully described below, that form inner fold 45 when the implant is in its relaxed configuration. Ends 42 and 43 have end surfaces 42a and 43a, respectively, that are generally flat, and substantially parallel, or perpendicular in other forms, to an axis X passing through the width of the implant in its relaxed configuration, wherein the ends may abut each other as seen in FIGS. 15A, 15B and 15E–15N. The ends of the implant may each alternatively abut the central portion of the implant, as shown for implants 60 and 70 in FIGS. 15C and 15D, respectively, to form a generally bi-lobed or binocular-shaped implant.

Figure 15D:
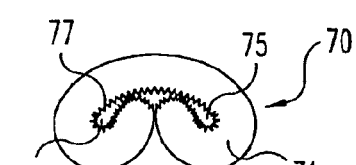
Figure 16D:
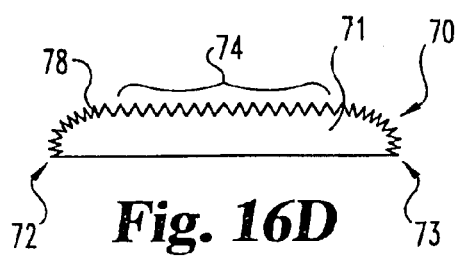
Figure 15E:
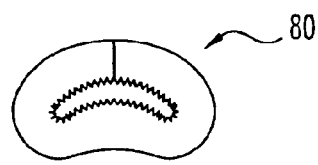
Figure 16E:
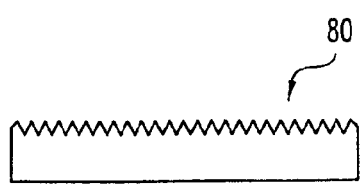
Figure 15F:
Figure 16F:
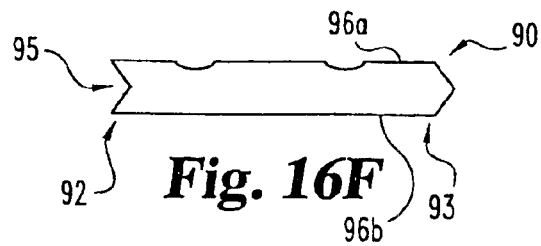
Figure 15G:
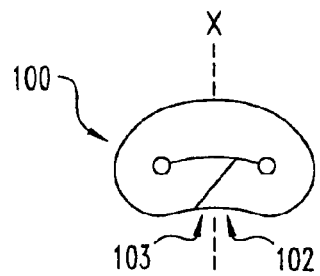
Figure 16G:
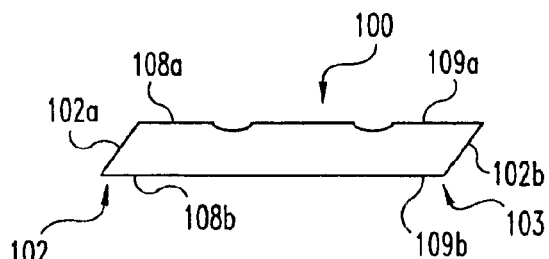
Figure 15H:
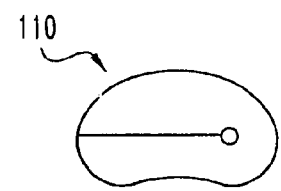
Figure 16H:
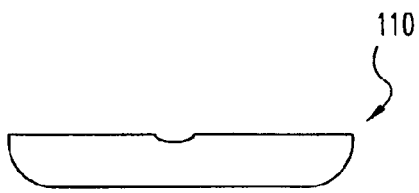
Figure 15I:
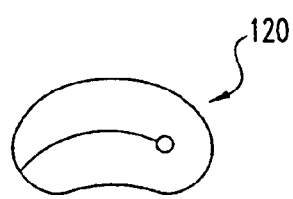
Figure 16I:
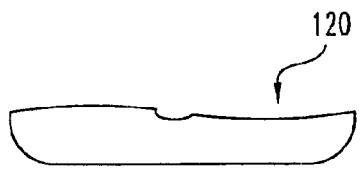
Figure 15J:
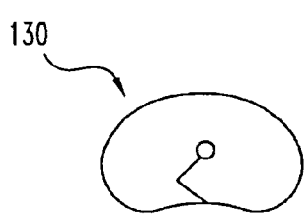
Figure 16J:
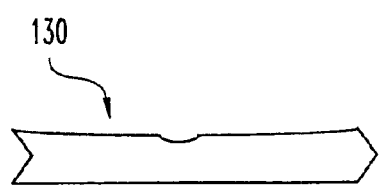
Figure 15K:
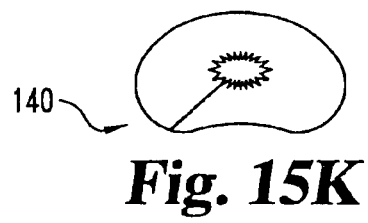
Figure 16K:
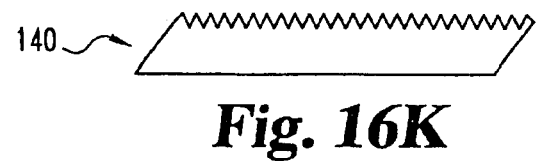
Figure 15L:
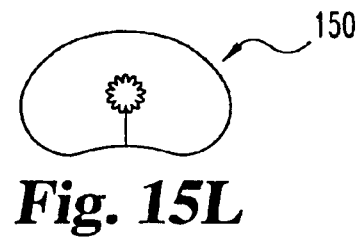
Figure 16L:
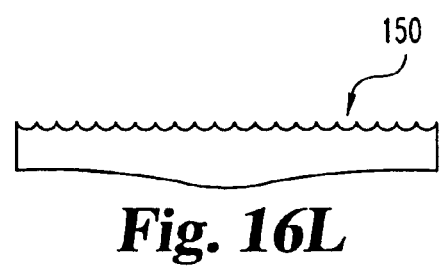
Figure 15M:
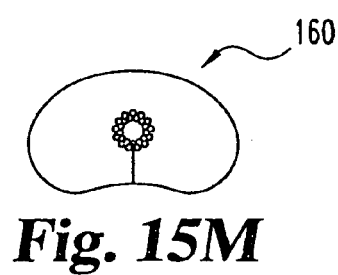
Figure 16M:
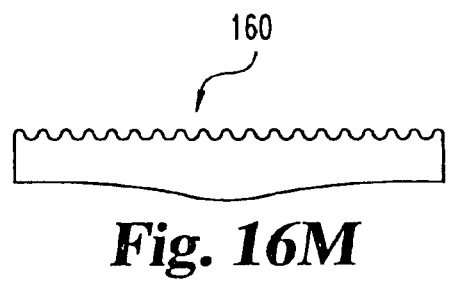
Figure 15N:
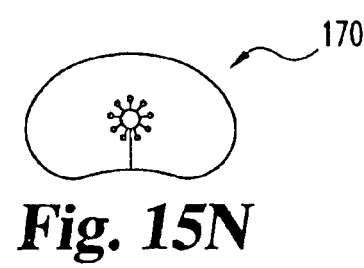
Figure 16N:
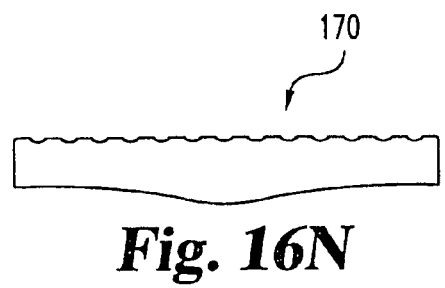

Alternatively, in other forms of the invention, one end of the implant may be tapered, or otherwise specifically shaped, and the other end may be shaped complementary to the tapered, or otherwise shaped, end. Moreover, either one or both sides 96a and 96b of the ends of the nucleus pulposus implant may be tapered. For example, and as seen in FIGS. 15F and 16F, both sides of end 93 of implant 90 are tapered to form a pointed end, such as a generally V-shaped end, that advantageously fits into a complementary-shaped (e.g., V-shaped) depression 95 defined by end 92. An implant having only one inner fold that defines one aperture and ends that are similarly configured as ends 92 and 93 is shown in FIGS. 15J and 16J. As another example, one side of each of the ends of the implant may be oppositely tapered as seen in FIGS. 15G and 16G. That is, side 108a of end 102 of implant 100 and opposite side 109b of end 103 are tapered as seen in FIG. 15G and 16G. End surfaces 102a and 102b of implant 100 are transverse to axis X when the implant is in its relaxed configuration shown in FIG. 15G. In those embodiments where the ends of the implants are tapered, or otherwise shaped, it is preferred that, when the ends of the implants contact each other or the central or other portion of the implant, an implant is formed that is uniform along the length of the implant through the region of contact.

Although the implant may assume a wide variety of shapes, it is typically shaped, in its folded, relaxed configuration, to conform to the shape of the natural nucleus pulposus.

In yet other forms of the invention, the folding implant may have a surface that includes surface projections that further aid in allowing short-term deformation of the implant without permanent deformation or other damage as described above. Referring now to FIGS. 15D and 16D, implant 70 includes a load bearing elastic body 71 having a first end 72, a second end 73 and a central portion 74. Inner fold 75 defines an aperture 76 and includes an inner fold surface 77 having wrinkles, or projections 78 thereon. Projections 78 of inner fold surface 77 extend into aperture 76. These wrinkles advantageously facilitate stretching of the implant without deformation, cracking, tearing, breakage, or other damage when the implant is straightened or elongated for insertion into the intervertebral disc space. In the embodiment shown in FIGS. 15D and 16D, the wrinkles, or surface projections, extend along the entire length of elastic body 71, including central portion 74. Other implants having wrinkled inner fold surfaces are seen in FIGS. 15E and 16E and other wrinkle configurations upon folding the implant are seen in FIGS. 15K–15N and 16K–16N.

In certain preferred forms of the invention, the apertures defined by the inner folds of the implants described above have a radius of at least about 1 mm. Moreover, in other preferred forms of the invention, a reinforcing material may be included at the inner fold surface to further improve the structural integrity of the implant. The reinforcing material may be a fabric that is either woven, or non-woven, and may be formed from braided fibers for further strength. The reinforcing material may be positioned on the inner fold surface, may project therefrom or may be entirely embedded under the inner fold surface. The implant may be formed as a single piece, or may be formed of more than one piece that is connected to the other pieces that form the assembled implant by fabric that may be made from braided or other fibers. Although these implants are designed to be used without an anchoring outer shell, they, as well as all of the implants described herein, may form the core elastic body of an implant that includes the outer shell described herein.

The implants may obtain their shape memory characteristics in a variety of ways. For example, the implants may be formed in a mold into a desired final shape, and, when deformed from this final shape by application of an external force, will return to the final shape upon release of the force.

Figure 17:
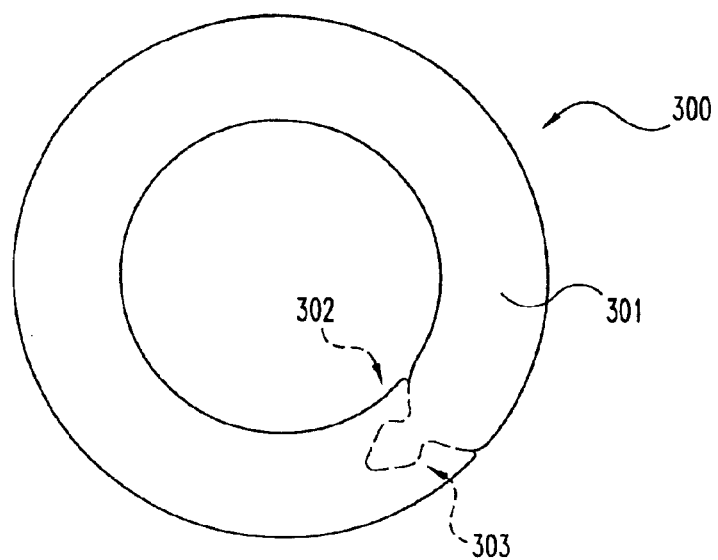
FIG. 17 depicts a top view of an alternative embodiment of a nucleus pulposus implant of the present invention having a self-locking feature. The implant is shown in its locked, relaxed configuration.
Figure 18:
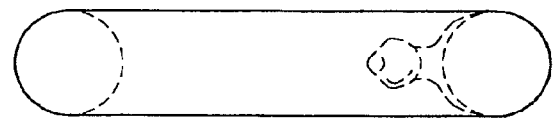
FIG. 18 depicts a side view of the implant of FIG. 17.
Figure 19:
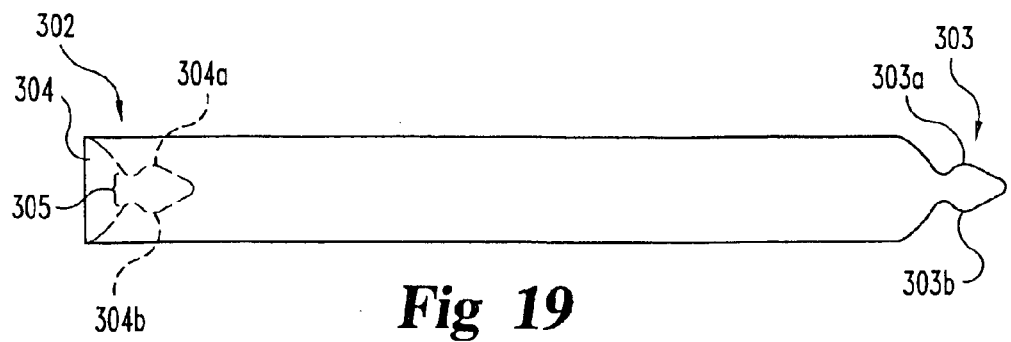
FIG. 19 depicts a side view of the implant of FIG. 18 in an unfolded, non-locked, non-relaxed configuration.

In yet another embodiment of the invention, a nucleus pulposus implant is provided that has a locking feature, with optional shape memory characteristics, and thus may also resist being expelled from the disc cavity to some extent. In one form of the invention as seen in FIGS. 17–19, an implant 300 includes a load bearing elastic body 301 having a first end 302 and a second end 303. The ends are typically configured for mating engagement with each other. Elastic body 301 has a first, locked configuration wherein first end 302 and second end 303 are matingly engaged to each other as seen more particularly in FIG. 17. When elastic body 301 has shape memory characteristics, elastic body 301 is deformable, manually, for example, into a second, substantially straightened, non-relaxed configuration for insertion into an intervertebral disc space, as seen in FIG. 19, and may automatically be configured or otherwise returned back into the first, locked, relaxed configuration after insertion due to its shape memory characteristics. In those cases where the elastic body does not have shape memory characteristics and the elastic body is configurable into a locked and/or straightened configuration, and in those cases where the elastic body has shape memory characteristics, the elastic body may also be placed into its locked configuration with the assistance of external force.

More particularly describing one form of the invention, end 302 defines an internal channel 304 as seen in FIG. 19 whereas end 303 is configured to conform to the shape of internal channel 304. The channel may take the form of a wide variety of shapes, as long as the ends of the elastic body may be matingly engaged to form a locked configuration. As seen in FIG. 19, the channel is somewhat hour-glass shaped. Manual, or other force, may be applied to end 303 so that it may be temporarily deformed, or configured, sufficiently to pass through narrowed passage 305 within internal channel 304. Once properly positioned, end 303 will be secured within channel 304, as end edges 303a and 303b are braced against channel edges 304a and 304b, respectively. Alternatively, one end of an implant with a locking feature may be friction-fit within the internal channel present in the other end of the implant. The friction-fit may arise as a result of the relative size differences between the inner diameter of the channel formed by one end and the outer diameter of the other end of the implant. Additionally, and/or alternatively, the outer surface of one end, and/or the inner surface of the channel defined by the other end, may include surface rougheings as described herein that aid in achieving the friction-fit. The implant may also be constructed from the biocompatible polymeric materials as described above.

When the implants are formed from an elastic material, such as a hydrogel, or other similar hydrophilic material, or include the resorbable outer shell, they may advantageously deliver desired pharmacological agents. The pharmacological agent may be a growth factor that may advantageously repair the endplates and/or the annulus fibrosis. For example, the growth factor may include a bone morphogenetic protein, transforming growth factor-β (TGF-β), insulin-like growth factor, platelet-derived growth factor, fibroblast growth factor or other similar growth factor or combination thereof having the ability to repair the endplates and/or the annulus fibrosis of an intervertebral disc.

The growth factors are typically included in the implants in therapeutically effective amounts. For example, the growth factors may be included in the implants in amounts effective in repairing an intervertebral disc, including repairing the endplates and the annulus fibrosis. Such amounts will depend on the specific case, and may thus be determined by the skilled artisan, but such amounts may typically include less than about 1% by weight of the growth factor. The growth factors may be purchased commercially or may be produced by methods known to the art. For example, the growth factors may be produced by recombinant DNA technology, and may preferably be derived from humans. As an example, recombinant human bone morphogenetic proteins (rhBMPs), including rhBMP 2-14, and especially rhBMP-2, rhBMP-7, rhBMP-12, rhBMP-13, and heterodimers thereof may be used. However, any bone morphogenetic protein is contemplated including bone morphogenetic proteins designated as BMP-1 through BMP-18.

BMPs are available from Genetics Institute, Inc., Cambridge, Mass. and may also be prepared by one skilled in the art as described in U.S. Pat. Nos. 5,187,076 to Wozney et al.; 5,366,875 to Wozney et al.; 4,877,864 to Wang et al.; 5,108,922 to Wang et al.; 5,116,738 to Wang et al.; 5,013,649 to Wang et al.; 5,106,748 to Wozney et al.; and PCT Patent Nos. WO93/00432 to Wozney et al.; WO94/26893 to Celeste et al.; and WO94/26892 to Celeste et al. All bone morphogenic proteins are contemplated whether obtained as above or isolated from bone. Methods for isolating bone morphogenetic protein from bone are described, for example, in U.S. Pat. No. 4,294,753 to Urist and Urist et al., 81 PNAS 371,1984.

In other forms of the invention, the pharmacological agent may be one used for treating various spinal conditions, including degenerative disc disease, spinal arthritis, spinal infection, spinal tumor and osteoporosis. Such agents include antibiotics, analgesics, anti-inflammatory drugs, including steroids, and combinations thereof. Other such agents are well known to the skilled artisan. These agents are also used in therapeutically effective amounts. Such amounts may be determined by the skilled artisan depending on the specific case.

The pharmacological agents are preferably dispersed within the hydrogel, or other hydrophilic, implant for in vivo release, and/or, with respect to the implants with the resorbable outer shell, may be dispersed in the outer shell. The hydrogel can be cross-linked chemically, physically, or by a combination thereof, in order to achieve the appropriate level of porosity to release the pharmacological agents at a desired rate. The agents may be released upon cyclic loading, and, in the case of implants including a resorbable outer shell, upon resorption of the shell. The pharmacological agents may be dispersed in the implants by adding the agents to the solution used to form the implant, by soaking the formed implant in an appropriate solution containing the agent, or by other appropriate methods known to the skilled artisan. In other forms of the invention, the pharmacological agents may be chemically or otherwise associated with the implant. For example, the agents may be chemically attached to the outer surface of the implant.

The implants described herein may have embedded therein small metal beads or wire for x-ray identification.

Methods of forming and implanting the nucleus pulposus implants described herein are also provided. In one form of the invention, with respect to implant 10 described above having the anchorable outer shell 30, implant 10 may be formed by first forming elastic body 15 and then forming the outer shell. Methods of forming elastic body 15 are well known in the art.

For example, if the elastic body is made of elastomeric materials, such as powdered elastomers including, for example, styrene-ethylene/butylene block copolymers, the powdered elastomer may be placed into an appropriate mold and may be compressed and heated to melt the powder. The mold is then cooled to room temperature. If the elastic body is made from a hydrogel, such as a polyvinyl alcohol, the polyvinyl alcohol powder may be mixed with a solvent, such as, for example, water or dimethylsulfoxide, or combinations thereof, and heated and shaken until a uniform solution is formed. The solution may then be poured into a mold, such as a rubber mold, and may be cooled at an appropriate temperature, such as about 0° C. to about −80° C., for several hours to allow for crystallization. After cooling, the hydrogel can be partially or completely hydrated by soaking and rinsing with water but, in certain preferred embodiments, may remain dehydrated so that it may be inserted through a smaller aperture in the annulus fibrosis.

Prior to positioning the implant in the interverterbral disc space, an incision may be made in the annulus fibrosis, or one may take advantage of a defect in the annulus, in order to remove the natural nucleus pulposus and any free disc fragments within the intervertebral disc space. The disc space is then distracted to a desired level. Once formed, and after preparing the disc space for receiving the implant, elastic body 15 may be implanted into the intervertebral disc space utilizing devices well known in the art and as described in U.S. Pat. Nos. 5,800,549 and 5,716,416. If the outer shell precursor material was already placed in the intervertebral disc space, excess precursor material may flow out of the disc space. This excess material should be promptly removed before it sets or otherwise cures. The outer shell material may be injected, or otherwise introduced, into the disc space utilizing devices that are well known in the art, such as syringes, sealant/caulk guns, automatic liquid injectors, and applicators that include, for example, two separate syringes which allow for simultaneous mixing of the components in a static mixer and delivery to the site, and may be injected either prior to or after introduction of the implant into the disc space. Whether the outer shell material is introduced prior to or after introduction of the implant into the disc space, the distractor is then removed, any excess precursor material seeping out of the disc space is removed and the precursor material within the disc space is cured to form the outer shell. It is noted that the elastic body may already be surrounded by the outer shell, which may be in a partially or fully hardened state but preferably remains deformable, prior to introducing the elastic body into the intervertebral disc space.

Figure 20:
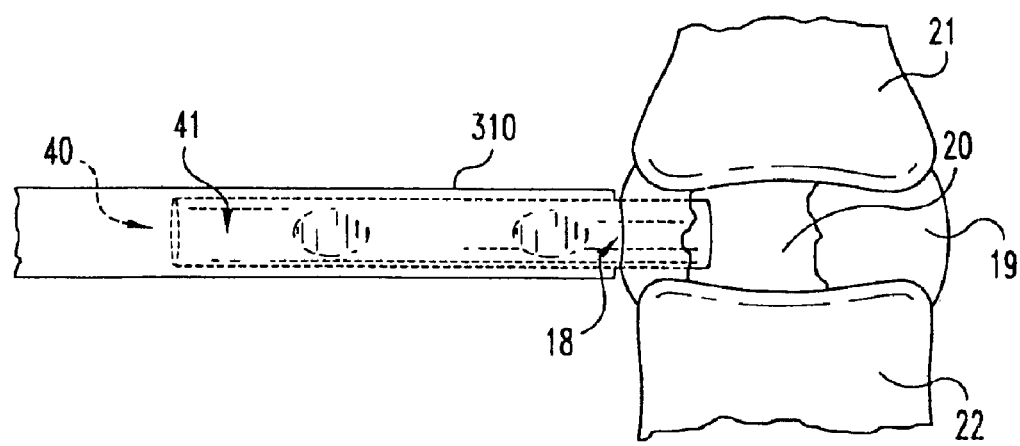
FIG. 20 depicts one step in a method of implanting nucleus pulposus implant 40 into intervertebral disc space 20 between vertebrae 21 and 22 using a conventional implantation tool 310.
Figure 21:
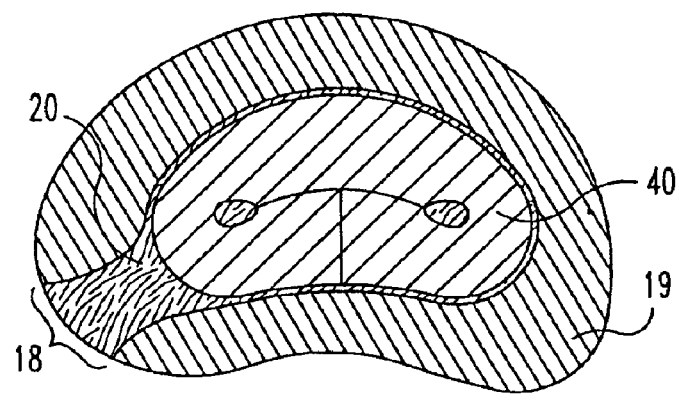
FIG. 21 depicts a top, cross-sectional view of a nucleus pulposus implant 10 in its folded, relaxed configuration positioned in intervertebral disc space 20.

In yet another form of the invention, a method for implanting a prosthetic intervertebral disc having shape memory is provided. In one embodiment, an implant including a load bearing elastic body having a first end and a second end positioned adjacent to a central portion to form at least one inner fold as described above is provided. The implant 40, for example, may be deformed by, for example, manual force into a substantially straightened, non-relaxed configuration for insertion through an aperture formed in the annular fibrosis as indicated in FIG. 20, and as best seen in FIG. 21. The aperture may be formed through deterioration or other injury to the annulus fibrosis, or may be made by purposely incising the annulus. The implant may then be positioned in a delivery tool 310 known in the art, such as that described in U.S. Pat. No. 5,716,416, and inserted through aperture 18 in annulus 19. As the implant enters the intervertebral space 20 and is no longer subject to manual force, it deforms back into its relaxed, folded configuration as seen in FIG. 21. A portion, or substantially all, of the natural nucleus pulposus may be removed from the intervertebral disc space, depending on the circumstances, prior to introduction of the implant into the intervertebral disc space. When implanting an implant that includes a locking feature, or other implant with shape memory as described herein, a similar protocol is followed. Additionally, with respect to an implant with a locking feature, the implant may be placed into the locked configuration with external force, imposed by, for example, medical personnel.

While the invention has been illustrated and described in detail in the drawings and foregoing description, the same is to be considered as illustrative and not restrictive in character, it being understood that only the preferred embodiment has been shown and described and that all changes and modifications that come within the spirit of the invention are desired to be protected. In addition, all references cited herein are indicative of the level of skill in the art and are hereby incorporated by reference in their entirety.

What is claimed is:

1. An intervertebral disc nucleus pulposus implant, comprising:
   (a) a load bearing elastic body positioned in an intervertebral disc space; and
   (b) a resorbable material partially or completely surrounding said load bearing elastic body and partially or substantially filling the remaining intervertebral disc nucleus space; wherein said resorbable material is uncured when introduced into the intervertebral disc space and thereafter cures after introduction into the intervertebral disc nucleus space.

2. The implant of claim 1, wherein said resorbable material is elastic after curing.

3. The implant of claim 1, wherein said resorbable material comprises a material selected from the group consisting of fibrin, albumin, gelatin, collagen, elastin, silk, demineralized bone matrix, polyethylene oxide, polyethylene glycol, polyvinyl alcohol, polypropylene fumarate and combinations thereof.

4. The implant of claim 1, wherein said elastic body is comprised of a hydrogel material.

5. The implant of claim 4, further including a pharmacological agent associated with said hydrogel material, said resorbable material, or a combination thereof, said agent selected from the group consisting of growth factors, anti-inflammatory drugs, antibiotics, analgesics, and combinations thereof.

6. The implant of claim 5, wherein said pharmacological agent is a growth factor.

7. The implant of claim 6, wherein said growth factor is selected from the group consisting of transforming growth factor β, bone morphogenetic proteins, fibroblast growth factors, platelet-derived growth factors, insulin-like growth factors and combinations thereof.

8. The implant of claim 7, wherein said growth factor is a recombinant human protein.

9. The implant of claim 4 wherein said hydrogel is a member selected from the group consisting of natural hydrogels, hydrogels formed from polyvinyl alcohol, acrylamides, polyacrylic acid, poly(acrylonitrile-acrylic acid), polyurethanes, polyethylene glycol, poly(N-vinyl-2-pyrrolidone), acrylates, poly(2-hydroxy ethyl methacrylate), copolymers of acrylates with N-vinyl pyrrolidone, N-vinyl lactams, acrylamide, polyurethanes and polyacrylonitrile.

10. The implant of claim 1, wherein said elastic body is comprised of a polymer selected from the group consisting of elastomers and hydrogels.

11. The implant of claim 1, wherein the outer surface of said elastic body includes projections extending therefrom, said projections configured for enhancing fixation of said body in said intervertebral space.

12. The implant of claim 1, wherein the outer surface of said elastic body is microtexturized.

13. The implant of claim 12, wherein said microtexturizing is performed by a process selected from the group consisting of bead blasting, plasma etching, chemical etching and combinations thereof.

14. The implant of claim 1, wherein the outer surface of said elastic body includes reactive chemical groups selected from the group consisting of hydroxyl groups, amino groups, carboxyl groups and organofunctional silane groups, said groups enhancing fixation of said elastic body to said resorbable shell.

15. The implant of claim 1 wherein said resorbable material is a tissue sealant or an adhesive.

16. The implant of claim 15 wherein said tissue sealant or adhesive is made from a material selected from the group consisting of fibrin, albumin, gelatin, collagen, elastin, silk, demineralized bone matrix, polyethylene oxide, polyethylene glycol, polyvinyl alcohol, polypropylene fumarate and combinations thereof.

17. The implant of claim 1 wherein said elastic body comprises a load bearing elastic body sized for placement in an intervertebral disc space, said body having a first end, a second end, a central portion, and a first configuration wherein said first end and said second end are positioned adjacent to said central portion to form at least one inner fold, said elastic body configurable into a second, straightened configuration for insertion through an opening in an intervertebral disc annulus fibrosis, said body configurable back into said first configuration after said insertion; wherein said body provides an implant having a substantially solid center when the body is in its first configuration.

18. The implant of claim 17 wherein said elastomer is selected from the group consisting of silicone, polyurethane, copolymers of silicone and polyurethane, polyolefins, nitrile and combinations thereof.

19. The implant of claim 1 wherein said elastic body comprises a load bearing elastic body having shape memory and sized for placement into an intervertebral disc space, said body having a first end, a second end, and a central portion; wherein said shape memory biases said body to a first configuration wherein said first end and said second end are positioned adjacent to said central portion to form at least one inner fold and to provide a substantially solid center core when the implant is in its first configuration; said elastic body configurable into a second, straightened configuration for insertion through an opening in an intervertebral disc annulus fibrosis; wherein said shape memory returns said body to said first configuration after said insertion; wherein said elastic body has a surface that includes wrinkles, indents or projections that relieve stress and prevent cracking or tearing of the implant when the implant is straightened for implantation.

20. The implant of claim 1 wherein said cured resorbable material anchors the implant in place to prevent migration in or from the disc space.

21. The implant of claim 1 wherein said cured resorbable material seals a defect in the annulus surrounding the intervertebral disc nucleus space.

22. The implant of claim 1 wherein said cured resorbable material compensates for the differences in geometry and size between the disc space and the implant.

23. The implant of claim 1 wherein said cured resorbable material is replaced by tissue after being resorbed.

24. The implant of claim 1 wherein said implant is wide enough to support adjacent vertebrae, and is of a height sufficient to separate adjacent vertebrae.

25. The implant of claim 1 wherein said implant has a volume of at least about 70% of the volume of the disc space.

26. The implant of claim 1 wherein said implant has a volume of at least about 90% of the volume of the disc space.

27. The implant of claim 1 wherein said hydrogel is a crosslinked hydrogel.

28. The implant of claim 1 wherein said elastic body comprises a hydrophilic polymer.

29. The implant of claim 1, wherein said elastic body comprises a member selected from the group consisting of silicone, polyurethane, copolymers of silicone and polyurethane, polyolefins, neoprene, nitrile, vulcanized rubber and combinations thereof.

30. The implant of claim 29 wherein said polyurethane is a member selected from the group consisting of thermoplastic polyurethanes, aliphatic polyurethanes, segmented polyurethanes, hydrophilic polyurethanes, polyether-urethane, polycarbonate-urethane and silicone polyether-urethane.

31. The implant of claim 1, wherein said elastic body comprises a member selected from the group consisting of glucomannan gel, hyaluronic acid, polysaccharides, crosslinked carboxyl-containing polysaccharides, and combinations thereof.

32. The implant of claim 1 wherein said elastic body has a compressive strength of between about 0.1 Mpa and about 20 Mpa.

* * * * *